United States Patent [19]

Liu et al.

[11] Patent Number: 5,914,448
[45] Date of Patent: Jun. 22, 1999

[54] PROCESS FOR THE PREPARATION OF ANTIVIRAL PLANT TRANSFORMED WITH LACTOFERRIN GENE

[75] Inventors: Jang-Ryol Liu; Kyung-Kwang Lee; Dae-Yeul Yu; Mi-Hee Lee, all of Daejeon, Rep. of Korea

[73] Assignee: Korea Institute of Science and Technology, Seoul, Rep. of Korea

[21] Appl. No.: 08/952,429

[22] PCT Filed: May 22, 1996

[86] PCT No.: PCT/KR96/00074

§ 371 Date: Nov. 17, 1997

§ 102(e) Date: Nov. 17, 1997

[87] PCT Pub. No.: WO96/37094

PCT Pub. Date: Nov. 28, 1996

[30] Foreign Application Priority Data

May 22, 1995 [KR] Rep. of Korea ............... 95-12724

[51] Int. Cl.[6] .................. A01H 5/00; C12N 5/10; C12N 15/82
[52] U.S. Cl. .................. 800/279; 435/418; 435/419; 800/288; 800/301; 800/317; 800/317.3
[58] Field of Search .................. 800/205, DIG. 43; 435/69.1, 172.3, 320.1, 419; 536/23.5

[56] References Cited

PUBLICATIONS

Mitra et al. Expression of a human lactoferrin cDNA in tobacco cells produces antibacterial protein(s). Plant Physiology. 106:977–981, Nov. 1994.

Lodge et al. Broad–spectrum virus resistance in transgenic plants expressing pokeweed antiviral protein. PNAS USA. 90(15):7089–7093, Aug. 1993.

"Proposed Mechanisms for the Involvement of Lactoferrin in the Hydrolysis of Nucleic Acids", TW Hutcherns et al., New York, 1994.

*Primary Examiner*—Douglas W. Robinson
*Assistant Examiner*—Thanda Wai
*Attorney, Agent, or Firm*—Anderson, Kill & Olick, P.C.

[57] ABSTRACT

A process for the preparation of an antiviral plant, which comprises transforming a plant with an expression vector containing a lactoferrin (Lf) gene and culturing the transformed plant.

5 Claims, 8 Drawing Sheets

SEQUENCE LISTING (1) GENERAL INFORMATION:

(iii) NUMBER OF SEQUENCES:  2

(2) INFORMATION FOR SEQ ID NO: 1:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: oligonucleotide DNA (xi) SEQUENCE DESCRIPTION: SEQ ID NO: 1:

AGTGGCTTGA GCGAAGG                                                    17

(2) INFORMATION FOR SEQ ID NO: 2:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: oligonucleotide DNA (xi) SEQUENCE DESCRIPTION: SEQ ID NO: 2:

GGCCGCGGTT TTACTTCCTG AGG                                             23

PROCESS FOR THE PREPARATION OF ANTIVIRAL PLANT TRANSFORMED WITH LACTOFERRIN GENE

This application is a 371 of PCT/KR96/00074, filed May 22, 1996.

FIELD OF THE INVENTION

The present invention relates to an antiviral plant producing lactoferrin and process for the preparation thereof. More specifically, it pertains to an antiviral plant producing lactoferrin, which is transformed with a lactoferrin (Lf) gene; a process for the preparation of the antiviral plant, which comprises transforming a plant with an expression vector containing a lactoferrin gene and culturing the transformed plant.

BACKGROUND OF THE INVENTION

Hitherto, various attempts have been made to develop a plant resistant to viral infection (hereinafter, an antiviral plant) by employing recombinant DNA technologies. For example, Powell Abel et al. introduced a cDNA encoding the coat protein of a virus to a plant (*Infect Immun.*, 35, 792–796 (1986)), while the introduction of a defective viral replicase to a plant was attempted by Anderson et al. (*P.N.A.S.*, 89, 8759–8763 (1992)). However, these methods are not practical in that, in order for a plant to have antiviral properties against a number of viruses, all the target viral genes must be introduced to the plant.

To solve this problem, Lodge et al. reported a method for conferring a general antiviral property on a plant by introducing thereto a gene encoding an antiviral protein, e.g., RIP (ribosome inhibiting protein) (*P.N.A.S.*, 90, 7089–7093 (1993)). Although the plant transformed by this method shows an antiviral activity against various viruses, there exists the problem that the antiviral protein may be harmful to human, and hence, the application of the above method may be restricted.

Lactoferrin is a conjugated protein found in mammals, e.g., in human milk, saliva, tear, semen and leukocyte. It affects the growth and differentiation of cells and has an antibacterial and immunopotentiative activity (Arold et al., *Science*, 197, 263–265 (1977)). Further, it shows an antiviral activity against Friend virus (Lu et al., *Cancer Res.*, 47, 4184–4188 (1987)), human immunodeficiency virus (HIV) and human cytomegalovirus (HCMV) (Meijer et al., *J. Disease*, 172, 380–388 (1995)).

Mitra and Zhang reported a method for providing a plant having an antibacterial activity by introducing thereto a cDNA encoding human lactoferrin (*Plant Physiol.*, 106, 977–981 (1994)). They confirmed the production of human lactoferrin in a tobacco cell by conducting a western blotting analysis of a tobacco cell transformed with human lactoferrin cDNA and anti-human lactoferrin antibody. They also reported that the proliferation of bacteria was significantly suppressed when the extract of the transformed tobacco cell was added to a culture of bacteria, e.g., Pseudomonas sp., which is pathogenic to tobacco. However, Mitra and Zhang did not, or failed to produce a transformed tobacco plant from the transformed tobacco cells. Moreover, human lactoferrin produced in the transformed tobacco cell was defective, i.e., significant parts thereof were missing, while the antibacterial activity was confirmed only in vitro. Accordingly, the question of whether or not an antiviral plant can be produced from a transformed tobacco cell was left unanswered in the prior art.

SUMMARY OF THE INVENTION

Accordingly, it is an object of the present invention to provide an antiviral plant producing lactoferrin.

Another object of the present invention is to provide a process for preparing said antiviral plant.

A further object of the present invention is to provide a process for producing lactoferrin in a plant.

In accordance with one aspect of the present invention, there is provided a process for preparing an antiviral plant producing lactoferrin, which comprises transforming a plant with an expression vector containing lactoferrin (Lf) gene.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE INVENTION

Figure 1:
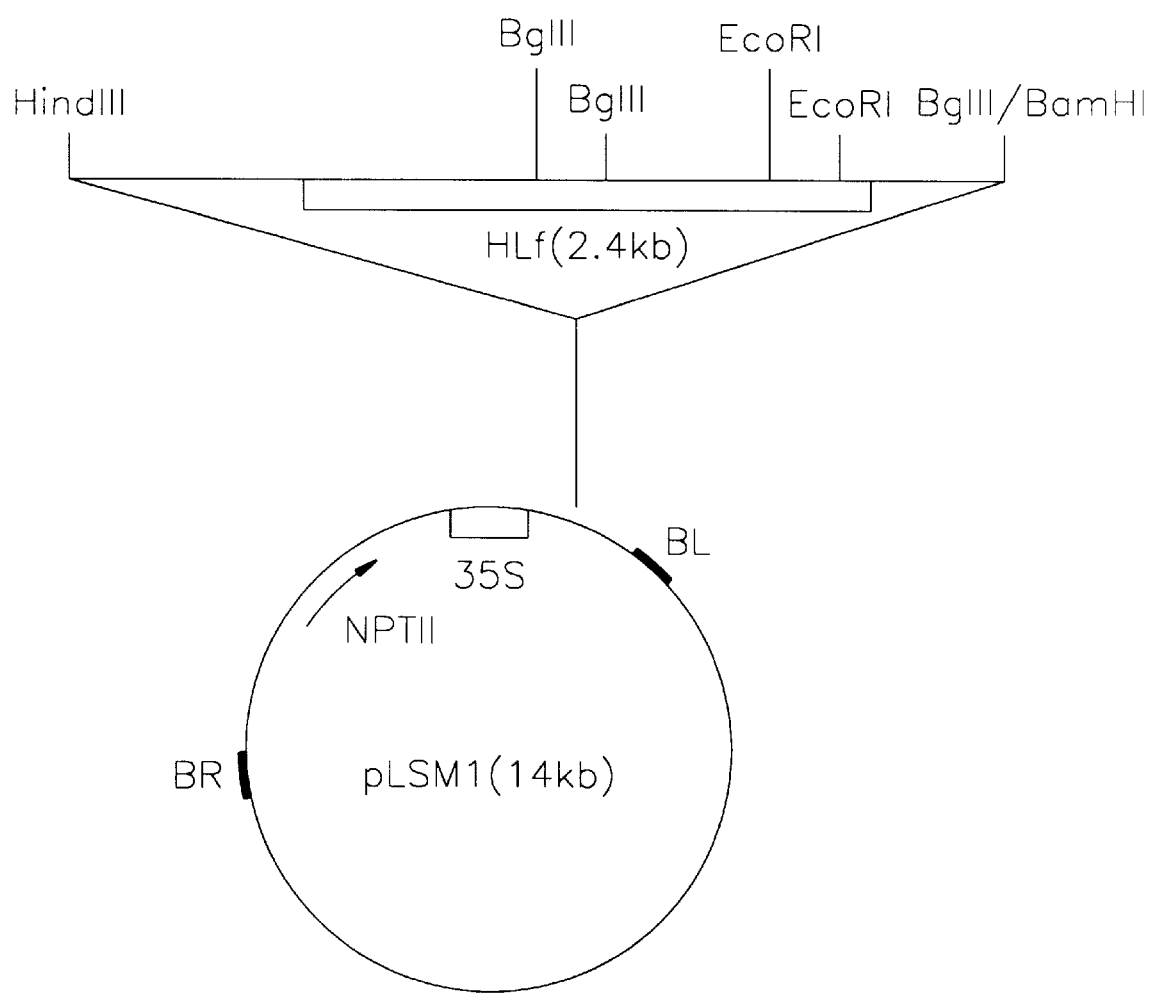
FIG. 1 shows the structure of plasmid pLSM1 comprising human lactoferrin (HLf) gene.

The present invention provides an antiviral plant producing lactoferrin and a process for preparing the antiviral plant, which comprises transforming a plant with an expression vector containing a lactoferrin (Lf) gene and culturing the transformed plant using a suitable medium.

The lactoferrin gene of the present invention may be any one of the mammalian lactoferrin genes, preferably, human lactoferrin gene (HLf). The lactoferrin gene may be prepared by a conventional chemical DNA synthesis method using the known nucleotide sequence of the lactoferrin gene. For instance, HLf gene may be chemically synthesized using the nucleotide sequence of HLf gene disclosed by, e.g., Powell and Ogden (*Nucleic Acids Research*, 18, 4013 (1990)). The lactoferrin gene of the present invention may also be obtained by digesting with suitable restriction enzymes a plasmid comprising the gene and, in case of human lactoferrin gene, it may be obtained by digesting with suitable restriction enzymes a plasmid, e.g., plasmid pBHL-1 wherein the HLf gene is inserted in plasmid pBSK (Yong-Yeon Cho, *Cloning of Human Lactoferrin Gene and Its Polymorphism in Normal and Cancer Cells*, August, 1993, a master's thesis in Science, Biology dept., Chungnam Univ., Korea). Any nucleotide substitution, deletion or addition in the nucleotide sequence of the lactoferrin gene may be made provided that the property and function thereof remains substantially unchanged.

On the other hand, an expression vector comprising the lactoferrin gene may be prepared in accordance with a conventional DNA manipulation technique, e.g., by inserting the gene to a suitable vector which may be selected from known vectors based on its compatibility with the intended host plant cell. For instance, the HLf gene prepared by digesting plasmid pBHL-1 with HindIII and BamHI may be inserted into the HindIII/BglII digestion site of a plant vector containing controllable CaMV (cauliflower mosaic virus) 35S promoter, e.g., plasmid pGA748 (*Pap. Am. Chem. Soc.,* 205 (1993)), to obtain plasmid pLSM1.

An Agrobacterium sp. cell may then be transformed with the expression vector prepared above in accordance with a conventional method, e.g., the freeze-thaw method of Holsters et al. (*Mol. Gen. Genet.,* 163, 181–187 (1978)). The transformed Agrobacterium may in turn be used to transform a plant cell by employing, e.g., the Agrobacterium-mediated transformation method described by Robert, B. H., et al. (*Plant Molecular Biology Manual,* A42, 1–9 (1988)).

Then, the resulting transformed plant cell may be cultured using a suitable medium, e.g., the MS (Murashige and Skoog) medium (*Physiol. Plant,* 15, 473–497 (1962)) which contains BAP (6-benzylaminopurine), NAA (naphthaleneacetic acid) and kanamycin. This medium induces shoot growth from the transformed plant cell. Then, the induced shoots may be further cultured using the MS medium containing kanamycin to induce roots. The resulting transformed plant shoot having a root may be transplanted in soil to obtain a complete plant having resistance against viral infection.

Suitable plants for use in the present invention include plants belonging to the family Solanaceae, e.g., a tobacco plant.

The antiviral plant prepared in the present invention produces an intact lactoferrin and shows an antiviral activity against the cucumovirus, e.g., CMV (cucumber mosaic virus).

Accordingly, the present invention also provides a process for producing lactoferrin in a plant, which comprises culturing a plant transformed with an expression vector containing a lactoferrin gene.

For instance, human lactoferrin may be mass-produced by culturing a plant transformed with an expression vector containing human lactoferrin gene, e.g., plasmid pLSM1.

The following Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

EXAMPLE 1

Preparation of Transformed Tobacco Producing Human Lactoferrin (Step 1)

A human lactoferrin (HLf) gene containing 3' and 5' UTRs (untranslated regions) (GenBank accession No.: UO7642), which was isolated from human mammary gland tissue cDNA library (Clontech, U.S.A.), was subcloned into the EcoRI site of plasmid pBluescript II SK (pBSK, Promega, U.S.A.) to construct a plasmid designated pBHL-1 (Yong-Yeon Cho, supra).

Plasmid pBHL-1 was digested with restriction enzymes HindIII and BamHI to obtain a 2.4 kb HLf gene. The HLf gene was inserted into the HindIII/BglII digestion site of plasmid pGA748 (*Pap. Am. Chem. Soc.,* 205 (1993)), said digestion site being downstream from the CaMV (cauliflower mosaic virus) 35S promoter site. The resulting plasmid was designated plasmid pLSM1 and its structure is shown in FIG. 1, wherein NPTII represents kanamycin resistant gene; 35S, CaMV 35S promoter; and HLf, human lactoferrin gene.

*E. coli* DH5α (Clontech) was transformed with plasmid pLSM1 in accordance with the CaCl$_2$ method (Cohen et al., *P.N.A.S.,* 69, 2110 (1972)). *E. coli* DH5α transformed with plasmid pLSM1 was deposited on May 10, 1995 with the Korean Collection for Type Cultures (KCTC) (Address: GERI, KIST, P.O. Box 115, Yusong, Taejon, 305–600, Republic of Korea) under the accession number of KCTC 0159BP in accordance with the terms of Budapest Treaty on the International Recognition of the Deposit of Microorganism for the Purpose of Patent Procedure.

Figure 2:
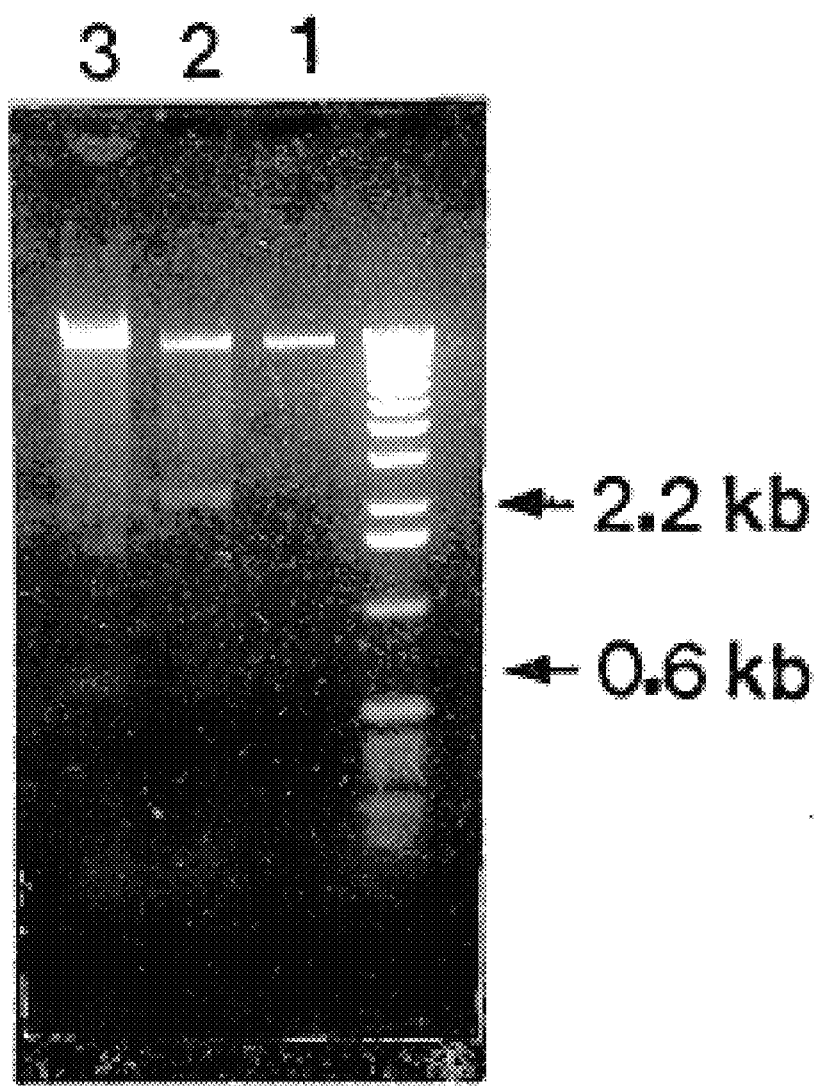
FIG. 2 depicts the result of restriction enzyme analysis of plasmids pGA748 and pLSM1.

The result of restriction enzyme analyses is shown in FIG. 2, wherein a 11.6 kb DNA fragment is observed when plasmid pGA748 is digested with EcoRI and HindIII (lane 1); a 11.8 kb DNA fragment and additional 2.2 kb DNA are observed when plasmid pLSM1 is digested with EcoRI and HindIII (lane 2); and, when plasmid pLSM1 is digested with BglII, which has a restriction site in the HLf gene segment, 13.4 kb and 0.6 kb DNA fragments are observed (lane 3) as expected from the restriction enzyme map. Lane M shows a standard DNA size marker.

(Step 2)

Plasmid pLSM1 was introduced to Agrobacterium LBA4404 (Clontech, U.S.A.) in accordance with the freeze-thaw method of Holsters et al. (*Mol. Gen. Genet.,* 163, 181–187 (1978)). The resulting transformed Agrobacterium LBA4404 was cultured together with leaf disks of a tobacco plant, *Nicotiana tabacum* L. Wisconsin 38, in order to transform the tobacco leaves with HLf gene, in accordance with the combination culture method (Horsch et al., *Science,* 227, 1229–1231 (1985)).

The transformed leaf disks were cultured in a shoot-inducing medium, i.e., MS (Murashige and Skoog) medium (*Physiol. Plant,* 15, 473–497 (1962)) containing 0.1 mg/l of BAP (6-benzylaminopurine), 1.0 mg/l of NAA (naphthaleneacetic acid), and 150 μg/ml of kanamycin. Selected shoots resistant to kanamycin were further cultured in the MS medium containing 200 μg/ml of kanamycin to obtain tobacco plants having roots.

(Step 3)

To investigate whether the tobacco shoots prepared above comprise HLf gene, polymerase chain reactions (PCR) were carried out in accordance with the method described by Edward et al. (*Nucleic Acids Res.,* 19, 1349 (1991)), wherein used are 100 mg each of the tobacco leaf disks and primers 1(5'-AGTGGCTTGAGCGAAGG-3') (SEQ ID NO:1) and 2(5'-GGCCGCGGTTTTACTTCCTGAGG-3') (SEQ ID NO:2) prepared based on the nucleotide sequence of the HLf gene described by Powell and Ogden (supra). The result is shown in FIG. 3.

Figure 3:
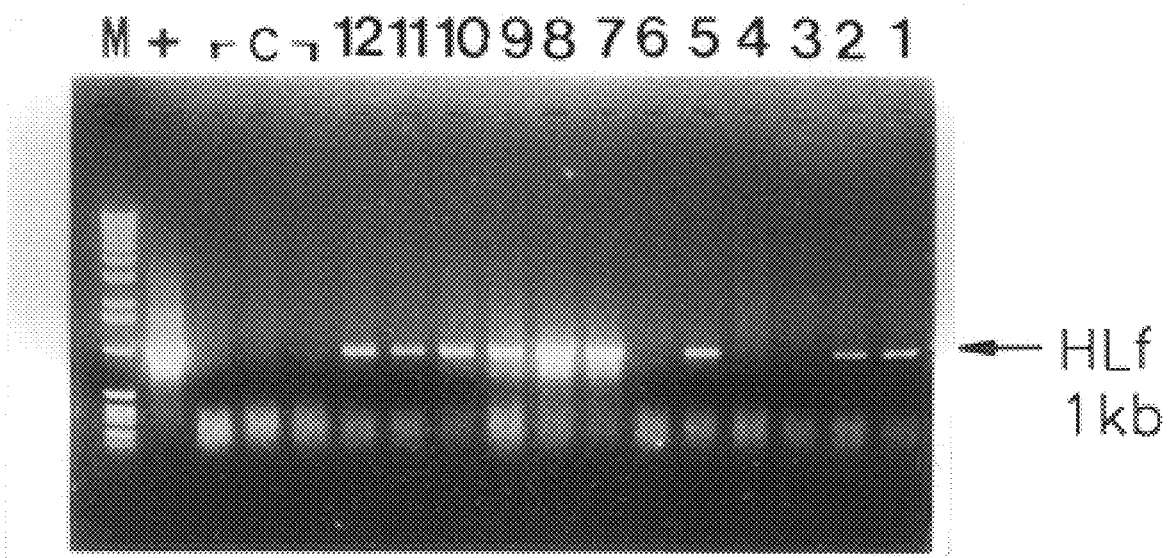
FIG. 3 displays the result of PCR analysis confirming the presence of HLf gene in the transformed tobacco shoots.

Observable in FIG. 3 are 1 kb-sized PCR bands associated with 9 out of the 12 plants tested, wherein lanes 1 to 12 represent the transformed tobacco plants; C, an untransformed tobacco plant; +, plasmid pLSM1; and M, standard DNA size markers.

(Step 4)

The transformants confirmed in (Step 3) were transplanted in soil and grown at 25° C. for 2 to 4 weeks under a 16-light hours/day condition. A 1 g leaf sample of each of the plants was ground and the genomic DNA was separated therefrom in accordance with the modified Shure's method (*Cell*, 35, 225–233 (1985)). Total RNA was also separated from the genomic DNA in accordance with the modified Sambrook's method (*Molecular Cloning: A Laboratory Manual*, 2nd Ed., pp 7.19–7.22, 1989, Cold Spring Harbor Laboratory Press, New York, U.S.A.) using CsCl.

10 $\mu$g each of the genomic DNA from each tobacco plant was digested with HindIII and subjected to a electrophoresis on 0.8% agarose gel. 40 $\mu$g each of the total RNA from each tobacco plant was electrophoresed on 1% agarose gel containing formaldehyde.

Figure 4:
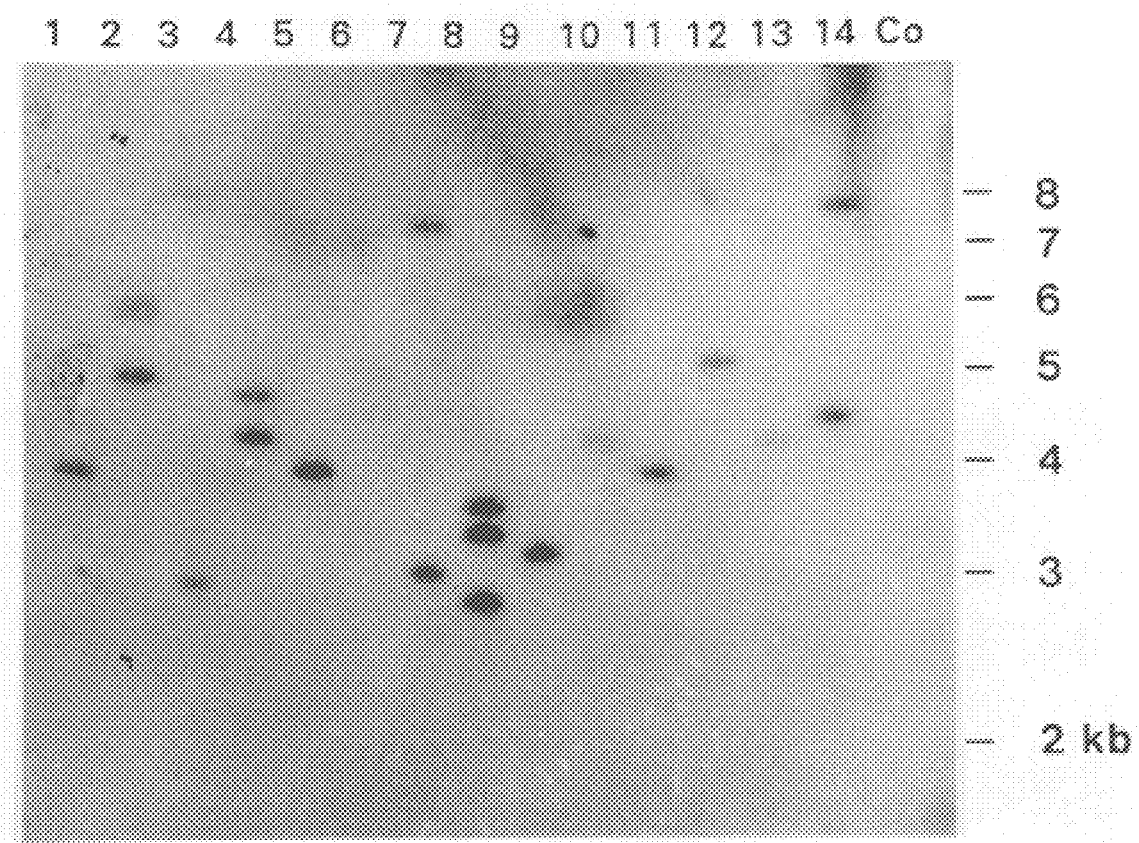
FIG. 4 provides the result of southern blot analysis confirming the presence of HLf gene in the transformed tobacco plants.
Figure 5:
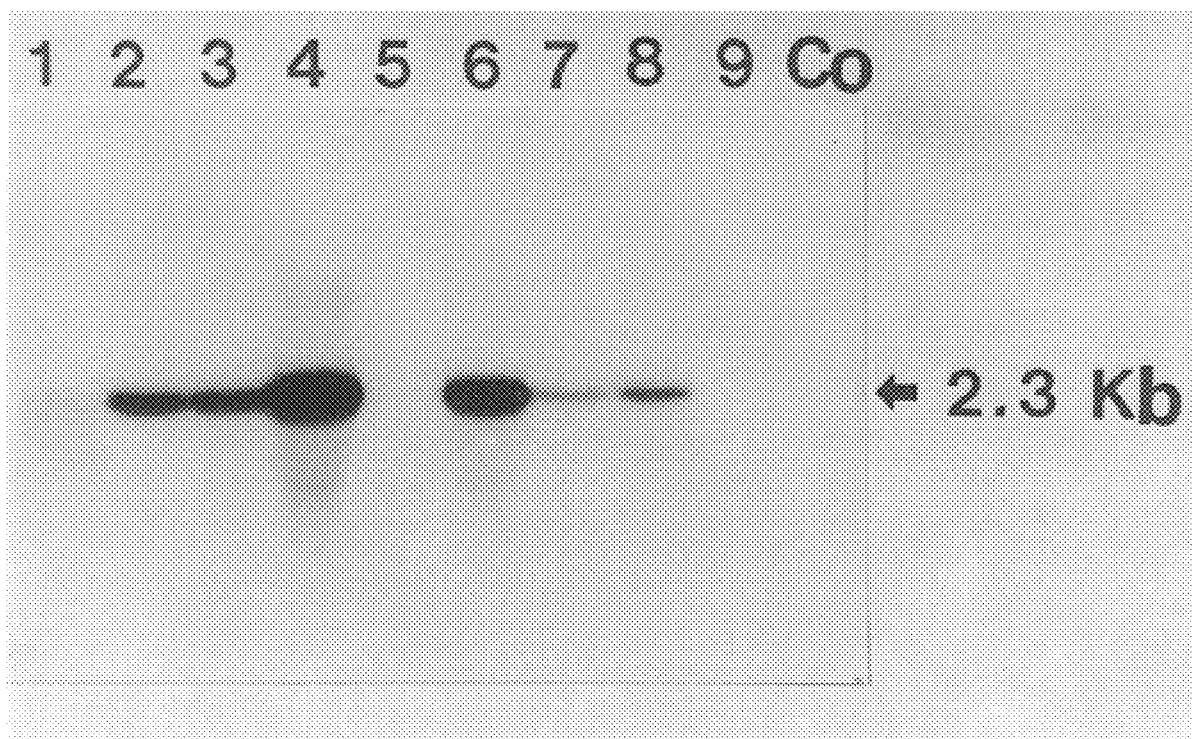
FIG. 5 presents the result of northern blot analysis confirming the expression of HLf gene in the transformed tobacco plants.

Each of the genomic DNAs and the total RNAs separated on the agarose gel was transferred to Nytran membrane (Schleicher & Schuell, Germany) and subjected to southern and northern blot analyses by using $^{32}$P-labelled HLf cDNA as a probe. It was confirmed by the southern blot analysis result that HLf gene was inserted in the genomic DNA of tobacco (FIG. 4). In FIG. 4, lanes 1 to 14 correspond to the transformants and Co, the untransformed tobacco. It was also confirmed by the northern blot analysis result that HLf gene was expressed in the transformants; various amount of 2.3 kb transcripts were observed in 8 out of the total 9 transformants (FIG. 5). In FIG. 5, lanes 1 to 9 correspond to the transformants and Co, the untransformed tobacco.

(Step 5)

A 100 mg leaf sample of selected transformed tobacco plants was ground and suspended in phosphate buffered saline (PBS) containing 1 mM phenylmethylsulfonyl fluoride (PMSF). The resulting suspension was centrifuged at 12,000 rpm for 10 min. to obtain a supernatant containing water-soluble proteins.

50 $\mu$g or 100 $\mu$g each of the water-soluble proteins was subjected to 10% SDS-PAGE by employing Laemmli's method (Nature 227, 680 (1970)). The proteins separated by size on the gel were transferred onto a nitrocellulose membrane (Hoefer) by employing an electrophoretic transferrer (Bio-Rad). The membrane was put into Tris-buffered saline (TBS) containing 3% bovine serum albumin (BSA) to block the unbound portion of the membrane. 300 ng of anti-HLf antibody (Sigma) in TBS containing 1% bovine serum albumin (BSA) was added to the membrane and reacted at room temperature for 2 hours to allow the binding of protein with the antibody.

The membrane was then washed with TBS, placed in an anti-human antibody solution, which was prepared by diluting goat anti-human IgG labeled with alkaline phosphatase (Sigma Co., U.S.A.) with 10,000-fold volume of TBS containing 1% BSA, and reacted at room temperature for 1.5 hour. The membrane was washed thoroughly with TBS and added thereto was 10 ml of BCIP/NBT (5-bromo-4-chloro-3-indolylphosphate/nitro blue tetrozorium) solution. The resultant was reacted at room temperature for 10 min. to develop a color reaction.

Figure 6:
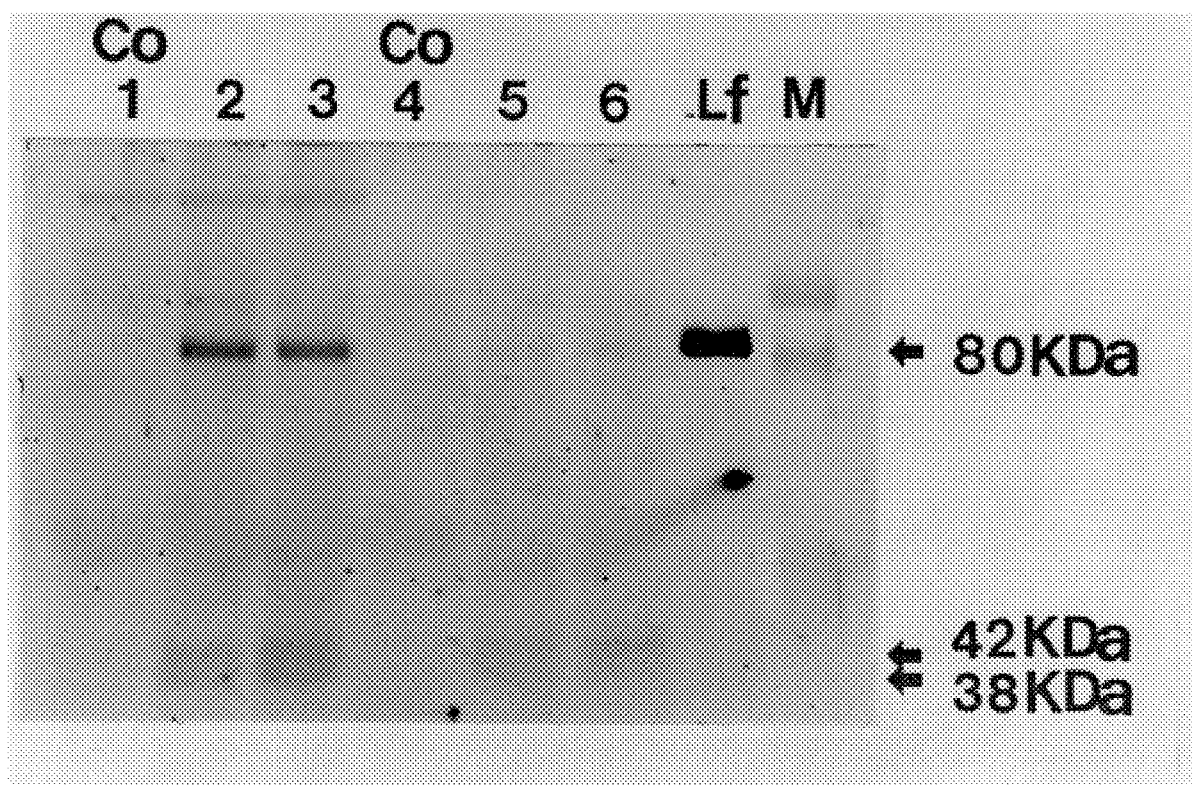
FIG. 6 exhibits the result of immuno blot analysis confirming the expression of HLf gene in the transformed tobacco plants.

The result in FIG. 6 shows that all transformants produced lactoferrin, while the untransformed tobacco did not. In FIG. 6, lanes 1 to 3 represent the result obtained with 100 $\mu$g protein samples, and lanes 4 to 6, 50 $\mu$g protein samples. Further, lanes 1 and 4 correspond to the untransformed tobacco and lanes 2, 3, 5 and 6, the transformed tobacco. The transformed tobacco plants produce not only a 80 kDa protein which is identical in size with human lactoferrin (Sigma) but also 38 or 42 kDa lactoferrin fragments.

EXAMPLE 2

Antiviral Activity of the Transformants (Step 1) First Viral Infection with CMV-Y Virus Three tobacco plants induced from untransformed leaf disk, one tobacco plant transformed with pGA748, and three tobacco plants transformed with pLSM1 were transplanted to soil and grown under the same condition as in (Step 4) of Example 1.

After 4 weeks from the transplantation, one new leaf from each plant was scratched with a carborundum powder, infected along a vein with a tobacco leaf suspension containing CMV-Y virus (*J. Gen. Virol.*, 74 (1), 319–322 (1993)), and, then, washed with water to remove the carborundum powder. One of the untransformed plants developed disease symptoms such as chlorosis, necrosis and systemic infection after 7 days from the viral infection, while all the other tobacco plants were healthy over 4 weeks after the viral infection.

(Step 2) Second Viral Infection with CMV-Y Virus

The six tobacco plants which remained healthy in (Step 1) were subjected to a second viral infection with 10 $\mu$g/ml of CMV-Y virus in accordance with the same procedure as in (Step 1). After 3 days from the infection, additional disease symptoms were observed in one of the two untransformed tobacco plants as well as in the tobacco plant transformed with plasmid pGA748, while one remaining untransformed tobacco plant and the three tobacco plants transformed with plasmid pLSM1 were healthy even after 2 weeks from the second infection.

(Step 3) Third Viral Infection with CMV-Y Virus

Figure 7:
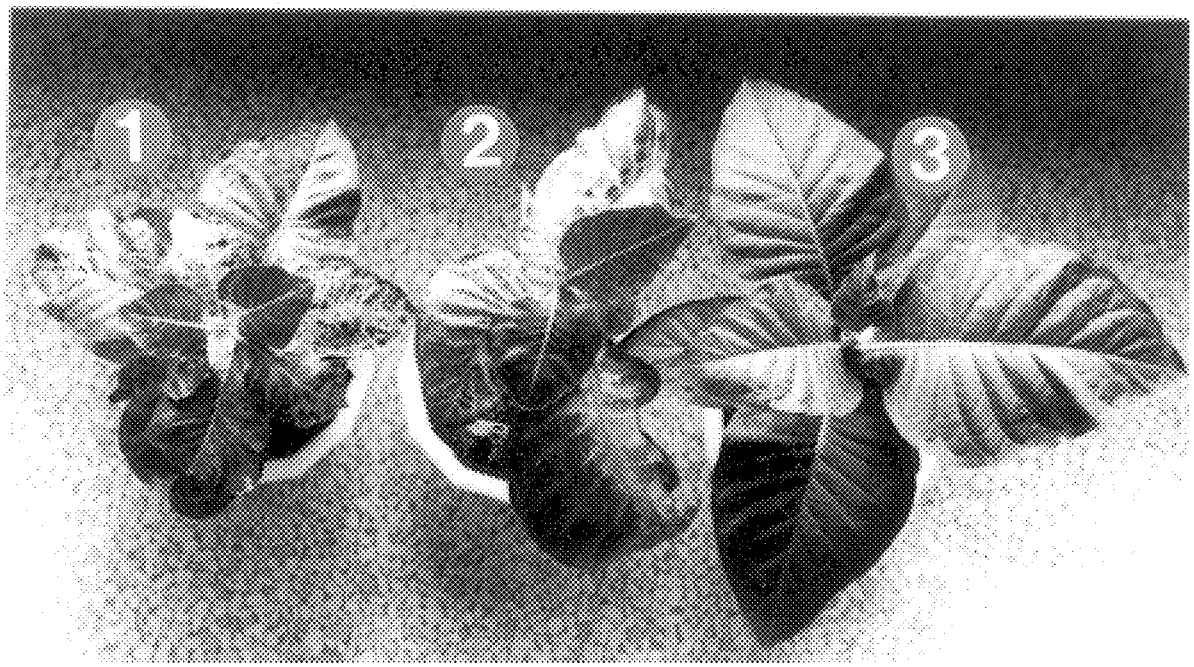
FIG. 7 shows the antiviral property of transformed tobacco plants after 4 weeks from viral infection.

One untransformed tobacco plant and three tobacco plants transformed with pLSM1, which remained healthy in (Step 2) were subjected to a third viral infection with 10 $\mu$g/ml of CMV-Y virus in accordance with the same procedure as in (Step 1). After 3 days from the infection, additional disease symptoms were observed in the untransformed tobacco plant, while three tobacco plants transformed with pLSM1 were healthy even after 2 weeks from the third infection and their growth rate were similar to those of uninfected tobacco plants (FIG. 7). In FIG. 7, 1 represents the untransformed tobacco plant; 2, tobacco plant transformed with plasmid pGA748; 3, tobacco plant transformed with plasmid pLSM1.

EXAMPLE 3

Antiviral Activity of the First Generation Progeny of the Transformant

The tobacco plants transformed with plasmid pLSM1 or pGA748 were self-pollinated to obtain seeds, and then, the transformants growing on MS medium containing 150 $\mu$g/ml kanamycin were selected. Those tobacco plants, which were transformed with plasmid pLSM1 and considered to have 1 copy of HLf gene shown in FIG. 4, lines 1 and 3, produced kanamycin resistant and kanamycin susceptible progenies in ratios of 140:48 and 90:30, respectively. This result shows that the antiviral character is inherited in a ratio of 3:1 in accordance with Mendelism.

Figure 8:
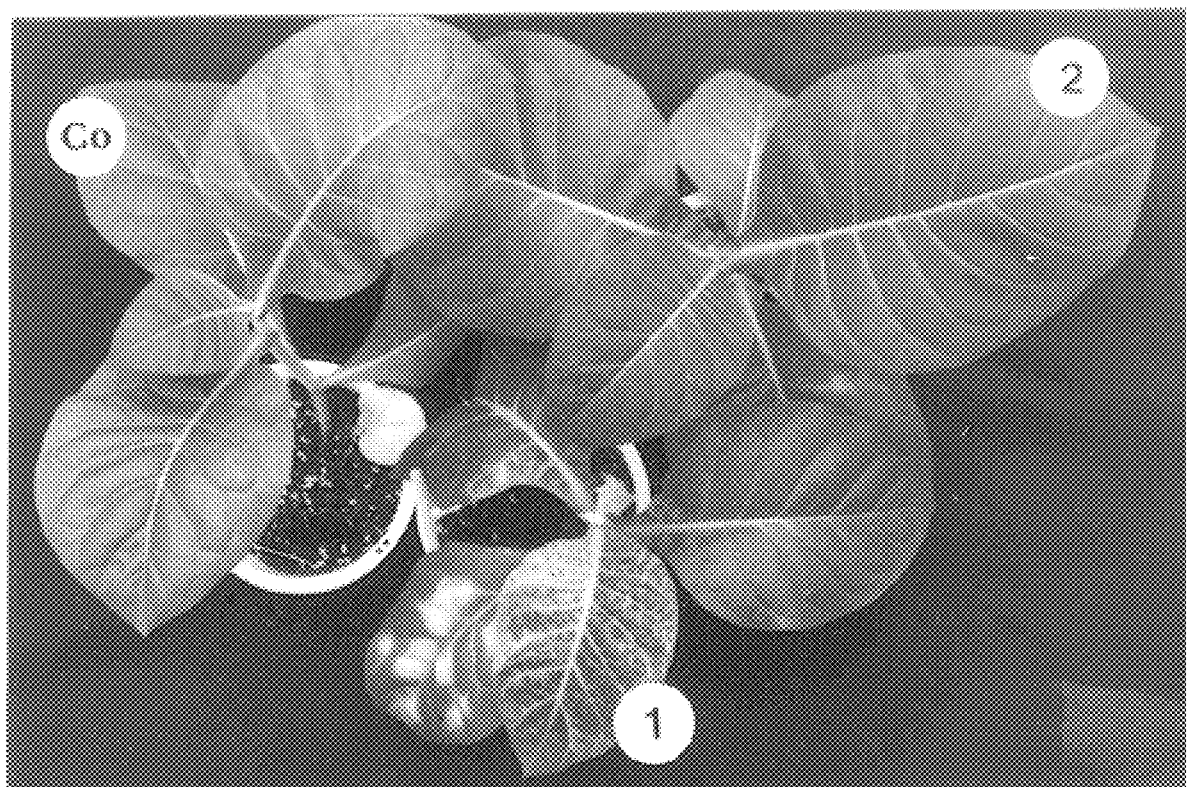
FIG. 8 illustrates the antiviral property of the first generation progenies of the transformed tobacco plants.

The kanamycin resistant progenies were transplanted in soil, grown at 25° C. for 2 to 4 weeks under a 16-light hours/day condition, and then, subjected to a viral infection in accordance with the same procedure as in (Step 6) of Example 1. The tobacco plants transformed with pGA748 showed disease symptoms at the third day from the infection. However, the tobacco plants transformed with pLSM1 exhibited localized, mild symptoms only on the infected leaf and a systemic infection was not observed even after 4 weeks from the infection. Further, they showed a growth rate similar to that of uninfected tobacco plants. The result is shown in FIG. 8, wherein 1 is a tobacco plant transformed with plasmid pGA748; 2, a tobacco plant transformed with plasmid pLSM1; and Co, an uninfected tobacco plant transformed with plasmid pGA748.

EXAMPLE 4
Preparation of Callus from Transformed Tobacco Plant

A callus was induced from the pLSM1-transformed tobacco progeny plant of Example 3 in accordance with the method of J. Draper et al. (*Plant Genetic Transformation and Gene Expression,* Chap. 2, 1988, Blackwell).

Specifically, a leaf sample from the tobacco progeny plant transformed with plasmid pLSM1 was treated with 0.5–1.0% of hypochlorite and washed several times with the sterilized water to remove the hypochlorite.

On the other hand, 2.0 mg/l of NAA and 0.5 mg/l of BAP were added to the MS medium and the mixture was autoclaved. 150 mg/l of kanamycin was added to the sterilized medium and aliquots of the resulting medium were placed in Petri dishes and solidified.

The disinfected leaf sample prepared above was cut by 0.5 cm×1 cm size and placed on the MS medium containing NAA, BAP and kanamycin in a Petri dish. The Petri dish was sealed and maintained at 25° C. in the dark. Two weeks after, undifferentiation of the leaf was observed; i.e., a callus was formed at the edge of the leaf pieces.

The callus was preserved on the same medium with subculturing monthly.

A callus of the tobacco plant transformed with plasmid pLSM1, i.e., *Nicotiana tabacum* W38 (pLSM1) was deposited on May 16, 1996 with the Korea Research Institute of Bioscience and Biotechnology, Korean Collection for Type Cultures (KCTC) (Address: KCTC, KRIBB, #52, Oundong, Yusong-ku, Taejon, 305–333, Republic of Korea) under the accession number of KCTC 0248BP in accordance with the terms of Budapest Treaty on the International Recognition of the Deposit of Microorganism for the Purpose of Patent Procedure.

An antiviral tobacco plant may be derived from the above callus by inducing shoot and root therefrom in accordance with the procedure of (Step 2) of Example 1, and then culturing the resulting plantlets in soil to develop into a whole plant (J. Draper et al., supra).

While the invention has been described with respect to the above specific embodiments, it should be recognized that various modifications and changes may be made to the invention by those skilled in the art which also fall within the scope of the invention as defined by the appended claims.

What is claimed is:

1. A process for preparing a transgenic plant which produces lactoferrin and exhibits antiviral activity against cucumovirus, the process comprising transforming a plant of the family Solanaceae with plasmid pLSM1 (KCTC 0159BP).

2. The process of claim 1, wherein the plant is a tobacco plant.

3. The process of claim 1, wherein the cucumovirus is cucumber mosaic virus.

4. A transgenic plant producing lactoferrin and exhibiting antiviral activity against cucumovirus, wherein the plant is prepared by transforming a plant of the family Solanaceae with plasmid pLSM1 (KCTC 0159BP).

5. A process for producing lactoferrin in a plant, the process comprising culturing plant cells of the family Solanaceae transformed with plasmid pLSM1 (KCTC 0159BP).

* * * * *